United States Patent
Webster et al.

(10) Patent No.: US 7,993,412 B2
(45) Date of Patent: Aug. 9, 2011

(54) NANOFIBERS AS A NEURAL BIOMATERIAL

(75) Inventors: Thomas J. Webster, Lafayette, IN (US); Janice L. McKenzie, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 1258 days.

(21) Appl. No.: 10/550,427

(22) PCT Filed: Mar. 26, 2004

(86) PCT No.: PCT/US2004/009104
§ 371 (c)(1),
(2), (4) Date: Oct. 5, 2006

(87) PCT Pub. No.: WO2004/096085
PCT Pub. Date: Nov. 11, 2004

(65) Prior Publication Data
US 2007/0038307 A1    Feb. 15, 2007

Related U.S. Application Data

(60) Provisional application No. 60/458,199, filed on Mar. 27, 2003.

(51) Int. Cl.
*A61F 2/02* (2006.01)
(52) U.S. Cl. .................................................. 623/23.73
(58) Field of Classification Search ............... 623/11.11, 623/23.72–23.76
See application file for complete search history.

(56) References Cited

U.S. PATENT DOCUMENTS

| | | | |
|---|---|---|---|
| 4,776,853 A | 10/1988 | Klement et al. | |
| 4,795,436 A | 1/1989 | Robinson | |
| 4,902,508 A | 2/1990 | Badylak et al. | |
| 4,998,239 A | 3/1991 | Strandjord et al. | |
| 5,281,422 A | 1/1994 | Badylak et al. | |
| 5,292,328 A | 3/1994 | Hain et al. | |
| 5,306,311 A | 4/1994 | Stone et al. | |
| 5,372,821 A | 12/1994 | Badylak et al. | |
| 5,415,704 A | 5/1995 | Davidson | |
| 5,573,784 A | 11/1996 | Badylak et al. | |
| 5,733,337 A | 3/1998 | Carr, Jr. et al. | |
| 5,744,515 A | 4/1998 | Clapper | |
| 6,106,913 A | 8/2000 | Scardino et al. | |
| 6,183,255 B1 | 2/2001 | Oshida | |
| 6,262,017 B1 | 7/2001 | Dee et al. | |
| 6,270,347 B1 | 8/2001 | Webster et al. | |
| 6,291,070 B1 | 9/2001 | Arpac et al. | |
| 6,319,264 B1 | 11/2001 | Tormala et al. | |
| 6,344,367 B1 | 2/2002 | Naya et al. | |
| 6,355,198 B1 | 3/2002 | Kim et al. | |

(Continued)

OTHER PUBLICATIONS

Dee et al., "Design and function of novel osteoblast-adhesive peptides for chemical modification of biomaterials," *J. Biomed. Mater. Res.*, 40:371-77 (1998).

(Continued)

*Primary Examiner* — Bruce E Snow
(74) *Attorney, Agent, or Firm* — Barnes & Thornburg LLP

(57) ABSTRACT

Nanomaterials for neural and orthopedic prostheses are disclosed. Composite carbon nanofibers enhance neuronal growth and minimize glial scar tissue formation. Methods and compositions to promote neuronal growth and minimize scar tissue formation during prolonged monitoring and treatment of neural tissue are disclosed. Composite polyurethane carbon nanofiber is a suitable material for neural implant. Composite carbon nanomaterials decrease adhesion of astrocytes and fibroblasts.

5 Claims, 13 Drawing Sheets

(a) 100:0 (PU:CN wt. %)

(b) 98:2 (PU:CN wt. %)

(c) 90:10 (PU:CN wt. %)

(d) 75:25 (PU:CN wt. %)

(e) 0:100 (PU:CN wt. %)

U.S. PATENT DOCUMENTS

| | | | |
|---|---|---|---|
| 6,368,859 | B1 | 4/2002 | Atala |
| 6,396,208 | B1 | 5/2002 | Oda et al. |
| 6,572,672 | B2 | 6/2003 | Yadav et al. |
| 6,669,706 | B2 | 12/2003 | Schmitt et al. |
| 6,670,179 | B1 * | 12/2003 | Mattson et al. ............... 435/325 |
| 6,689,374 | B2 | 2/2004 | Chu et al. |
| 6,756,286 | B1 | 6/2004 | Moriceau et al. |
| 6,790,455 | B2 | 9/2004 | Chu et al. |
| 6,797,514 | B2 | 9/2004 | Berenson et al. |
| 6,805,898 | B1 | 10/2004 | Wu et al. |
| 6,881,249 | B2 | 4/2005 | Anderson et al. |
| 6,929,539 | B2 | 8/2005 | Schutz et al. |
| 2002/0167118 | A1 | 11/2002 | Billiet et al. |
| 2002/0173033 | A1 | 11/2002 | Hammerick et al. |
| 2002/0173213 | A1 | 11/2002 | Chu et al. |
| 2003/0040809 | A1 | 2/2003 | Goldmann et al. |
| 2003/0050711 | A1 | 3/2003 | Laurencin et al. |
| 2004/0028875 | A1 | 2/2004 | Van Rijn et al. |
| 2004/0104672 | A1 | 6/2004 | Shiang et al. |
| 2004/0131753 | A1 * | 7/2004 | Smith et al. .................... 427/2.1 |
| 2004/0171323 | A1 | 9/2004 | Shalaby |
| 2004/0241211 | A9 | 12/2004 | Fischell et al. |
| 2006/0173471 | A1 | 8/2006 | Carr, Jr. et al. |

OTHER PUBLICATIONS

Webster et al., "Specific proteins mediate enhanced osteoblast adhesion on nanophase ceramics," *J. Biomed. Mater. Res.*, 51:475-83 (2000).

Webster et al., "Enhanced functions of osteoblasts on nanophase ceramics," *Biomaterials*, 21:1803-10 (2000).

Curtis & Wilkinson, "Review. Topographical control of cells," *Biomaterials*, 18(24):1573-83 (1997).

Puleo & Bizios, "RGDS tetrapeptide binds to osteoblasts and inhibits fibronectin-mediated adhesion," *Bone*, 12:271-76 (1991).

Siegel, "Creating nanophase materials," *Scientific American*, 275(6):74 (1996).

Webster et al., "Design and evaluation of nanophase alumina for orthopaedic/dental applications," *Nanostructured Materials*, 12:983-86 (1999).

Webster et al., "Enhanced surface and mechanical properties of nanophase ceramics to achieve orthopaedic/dental implant efficacy," *Key Engineering Materials*, vols. 192-195, pp. 321-24 (Proceedings of the 13th international symposium on ceramics in medicine, Bologna, Italy, 2000 (Trans Tech Publications, 2001).

Webster et al., "Mechanisms of enhanced osteoblast adhesion on nanophase alumina involve vitronectin," *Tissue Engineering*, 7(3):291-301 (2001).

Webster et al., "Nanoceramic surface roughness enhances osteoblast and osteoclast functions for improved orthopaedic/dental implant efficacy," *Scripta Mater.*, 44:1639-42 (2001).

Jean-Louis Pariente et al., "In vitro biocompatibility assessment of naturally derive and synthetic biomaterials using normal human urothelial cells," *J. Biomed. Mater. Res.*, 55(1), (2001), pp. 33-39.

Malachy J. Gleeson et al., "The use of alloplastic biomaterials in bladder substitution," *J. Urol.*, 148, (1992), pp. 1377-1382.

Janeta Nikolovski et al., Smooth muscle cell adhesion to tissue engineering scaffolds, *Biomat.*, 21, (2000), pp. 2025-2032.

Anthony Atala et al., "Implantation in vivo and retrieval of artificial structures consisting of rabbit and human urothelium and human bladder muscle," *J. Urol.*, 150, (1993), pp. 608-612.

M. J. Lyndon et al., "Cellular interactions with synthetic polymer surfaces in culture," *Biomat.* 6, (1985), pp. 396-402.

A. S. G. Curtis et al., "Adhesion of cells to polystyrene surfaces," *J. Cell Biol.*, 97, (1983), pp. 1500-1506.

Joseph A. Chinn et al., "Enhancement of serum fibronectin adsorption and the clonal plating efficiencies of Swiss mouse 3T3 fibroblast and MM14 mouse myoblast cells on polymer substrates modified by radiofrequency plasma deposition," *J. Colloid Interface Sci.*, 127, (1989), pp. 67-87.

Paul Goldhaber, "The influence of pore size on carcinogenicity of subcutaneously implanted Millipore filters," *Proc. Am. Assoc. Cancer Res.*, 3 (1961), p. 28.

J. Brauker et al., "Neovascularization of immunoisolation membranes: the effect of membrane architecture and encapsulated tissue," *Transplant Proc.*, 24, (1992); p. 2924.

Paul Weiss, "In vitro experiments on the factors determining the course of the outgoing nerve fiber," *J. Exp. Zool.*, 68, (1945), pp. 393-448.

G. A. Dunn et al., "Alignment of fibroblasts on grooved surfaces described by a simple geometric transformation," *J. Cell Sci.*, 83, (1986), pp. 313-340.

J. Meyle et al., "Variation in contact guidance by human cells on a microstructured surface," *J. Biomed. Mater. Res.*, 29, (1995), pp. 81-88.

John A. Schmidt et al., "Macrophage response to microtextured silicone," *Biomat.*, 12, (1992), pp. 385-389.

Karen M. Haberstroh et al., "The effects of sustained hydrostatic pressure on select bladder smooth muscle cell functions," *J. Urol.*, 162, (1999), pp. 2114-2118.

Jinming Gao et al., "Surface hydrolysis of poly(glycolic acid) meshes increases the seeding density of vascular smooth muscle cells," *J. Biomed. Mat. Res.*, 42, (1998), pp. 417-424.

Mark A. Schubert et al., "Role of oxygen in biodegradation of poly(etherurethane urea) elastomers," *J. Biomed. Mat. Res.*, 34, (1997), pp. 519-530.

Thomas J. Webster et al., "Osteoblast adhesion on nanophase ceramics," *Biomaterials*, 20, (1999), pp. 1221-1227.

M. Conley et al., "Effects of biodegradable polymer particles on rat marrow-derived stromal osteoblasts in vitro," *Biomaterials*, 19, (1998), pp. 1255-1268.

Susan L. Ishaug-Riley et al., "Three-dimensional culture of rat calvarial osteoblasts in porous biodegradable polymers," *Biomaterials* 19, (1998), pp. 1405-1412.

Susan L. Ishaug-Riley et al., "Human articular chondrocyte adhesion and proliferation on synthetic biodegradable polymer films," *Biomaterials*, 20, (1999), pp. 2245-2256.

Laurence S. Baskin et al., "Cellular Signaling in the Bladder," www.bioscience.org., *Frontiers in Bioscience*, 2, d592-595, (1997), 8 pgs.

Gunilla Dahlfors et al., "Vascular Endothelial Growth Factor and Transforming Growth Factor-β1 Regulate the Expression of Insulin-Like Growth Factor-Binding Protein-3, -4, and -5 in Large Vessel Endothelial Cells," *The Endocrinology Society*, vol. 141, No. 6, (2000), pp. 2062-2067.

Antonios G. Mikos et al., "Preparation and Characterization of poly(L-lactic acid) foams," *Polymer*, vol. 35, No. 5, (1994), pp. 1068-1077.

Kenjiro Yamakawa et al., "Peroxisome Proliferator-Activated Receptor-γ Agonists Increase Vascular Endothelial Growth Factor Expression in Human Vascular Smooth Muscle Cells," *Biochemical and Biophysical Research Communications*, 271, (2000), pp. 571-574.

Young-Jo Kim et al., "Fluorometric Assay of DNA in Cartilage Explants Using Hoechst 33258," *Analytical Biochemistry*, 174, (1988), pp. 168-176.

Kari I. Kivirikko et al., "Modifications of a Specific Assay for Hydroxyproline in Urine," *Analytical Biochemistry*, 19, (1967), pp. 249-255.

C. B. Wilson et al., "Extracellular matrix and integrin composition of the normal bladder wall," *World J Urol.* 14, (1996), pp. S30-S37.

Paul Weiss, "Experiments on Cell and Axon Orientation in Vitro: The Role of Colloidal Exudates in Tissue Organization," Journal of Experimental Zoology, vol. 100(3), (1943), pp. 353-386.

Int'l Search Report, PCT/US04/09104, Mar. 2004.

Written Opinion, PCT/US04/09104, Mar. 2004.

\* cited by examiner (a) 100:0 (PU:CN wt. %)

(b) 98:2 (PU:CN wt. %)

(c) 90:10 (PU:CN wt. %)

(d) 75:25 (PU:CN wt. %)

(e) 0:100 (PU:CN wt. %)

a) 100:0 (PU:CN wt. %)*

(b) 98:2 (PU:CN wt. %)*

(c) 90:10 (PU:CN wt. %)**

(d) 75:25 (PU:CN wt. %)**

(e) 0:100 (PU:CN wt. %)*

(a) Conventional (200 nm) with a low surface energy (c) Nanophase (100 nm) with a low surface energy (d) Nanophase (60 nm) with high surface energy (a) Composition is 100:0 (PCU:CN) wt. %

(b) Composition is 98:2 (PCU:CN) wt. %

(c) Composition is 90:10 (PCU:CN) wt. %

(d) Composition is 75:25 (PCU:CN) wt. %

High surface e nergy carbon n anofibers in polymer without an applied electric field High surface energy carbon nanofibers in polymer with an applied electric field

NANOFIBERS AS A NEURAL BIOMATERIAL

This application claims priority to U.S. Ser. No. 60/458,199 filed 27 Mar. 2003.

GOVERNMENT RIGHTS

Research relating to this invention was supported in part by the U.S. Government under Grant No. DM10232597 awarded from the National Science Foundation. The U.S. Government may have certain rights in this invention.

FIELD

This disclosure generally relates to implantable neural and orthopedic devices having therein or thereon a nanomaterial.

BACKGROUND

Many orthopedic implants are made of vanadium steel, stainless steel, cobalt alloys, titanium, gold and amalgams (a metal alloy containing mercury). For neural implants, silicon is most widely used.

A healing response that follows an implantation, impacts the long-term functionality of the implanted device. The prolonged healing process recruits a variety of body fluids, proteins, and unwanted cell types to the tissue-implant interface. Healing characteristics common to unsuccessful bone and neural prosthetic wound-healing include prolonged fibrous encapsulation and chronic inflammation.

Extensive scar tissue formation is a common occurrence that leads to implant failure for an orthopedic implant juxtaposed to bone or a neural implant with the conductive neural tissue. With regard to orthopedic implants, fibrous encapsulation (or callus formation) at the tissue-implant interface decreases the effectiveness of the implant's bonding to bone and often results in clinical failures. With regard to neural implants, glial scar-tissue forms around probes implanted into the central nervous system. The glial scar response, gliosis, includes the formation of cells, for example astrocytes, which encapsulate the probes with non conductive tissue. Gliosis inhibits the ability of the probes or any other implants to properly interact with the surrounding neural tissue.

SUMMARY

Methods and compositions that comprise a nanomaterial as a suitable biocompatible material for neural and orthopedic implants are disclosed. Methods to minimize glial scar tissue formation or fibroblast encapsulation due to prolonged use of implants are disclosed. The carbon nanofibers in a neural or an orthopedic implant range in size of about 2 to 200 nm. The nanomaterial can comprise a composite carbon nanofiber-polyurethane matrix. The matrix may be selected from the group consisting of polyurethane, polymethacrylate, polyester, polyvinyl and any copolymers thereof. The nanomaterial may be applied to or made a part of the surface of the implant.

More specifically with regard to a neural implant, the implant can be a device coated with a nanomaterial. The neural implant can be a device with at least one component of the device made of a nanomaterial. The neural implant can comprise carbon nanofibers. The neural implant can have the carbon nanotubes functionalized. The neural implant can have the carbon nanotubes aligned.

The neural implant may be a neural probe. The neural implant may be a prostheses that includes an implantable device with a composite polyurethane carbon nanotube, the device capable of stimulating neuronal growth and minimizing glial scar tissue formation. The neural prostheses has carbon nanotubes which form 2% to 100% of the composite.

One suitable method for minimizing scar formation caused by a neural implant includes obtaining a neural implantable device; coating the implantable device with a nanomaterial; and securing the implantable device in the neural tissue.

One suitable method of stimulating neuronal growth and minimizing scar formation by an implant in a brain can comprise obtaining a neural implantable device comprising a nanomaterial; securing the implantable device in the brain; and providing neuronal stimulants through the device.

The orthopedic prostheses can comprise an implantable device coated with a composite polyurethane carbon nanotube, capable of stimulating osteoblast proliferation and minimizing fibroblast encapsulation.

One suitable method of stimulating osteoblast proliferation and minimizing fibroblast encapsulation by an orthopedic implant; comprises obtaining an orthopedic implantable device comprising a nanomaterial; and securing the implantable device.

One suitable method of selecting a nanomaterial suitable for implant, comprises determining structural dimensions of a biological molecule in a biological tissue; and fabricating the nanomaterial whose surface structural dimension is similar to the biological molecule.

A method of selecting a nanomaterial, wherein the biological molecule is laminin, is disclosed.

BRIEF DESCRIPTION OF THE DRAWINGS

The drawings are provided to illustrate some of the embodiments of the disclosure. It is envisioned that alternate configurations of the embodiments of the present disclosure maybe adopted without deviating from the disclosure as illustrated in these drawings.

DETAILED DESCRIPTION OF THE DISCLOSURE

Figure 1:
FIG. 1 illustrates the representative Scanning Electron Microscope (SEM) images of polyurethane: carbon nanotube (PU:CN) composites. Scale bar=1 μm. (Sigma), and counted using fluorescence microscopy (365 nm excitation and 400 nm emission wavelengths).
Figure 1:
Figure 1:
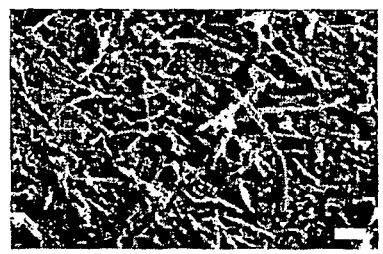
Figure 1:
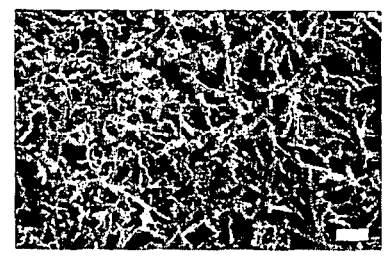
Figure 1:
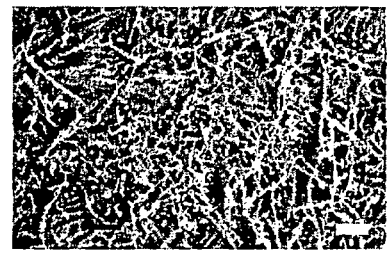

While the concepts of the present disclosure are illustrated and described in detail in the drawings and the description below, such an illustration and description is to be considered as exemplary and not restrictive in character, it being understood that only the illustrative embodiment is shown and described and that all changes and modifications that come within the spirit of the disclosure are desired to be protected.

As used herein nanotubes, nanoparticles, nanofibers, nanowires, and nanophase material refer to nanomaterials whose size range is from 1 nm to less than 1 µM. In otherwords, the nanomaterials have a size range in nanometers ($10^{-9}$ m). As used herein, the term nanomaterial may also include a nanocomposite that includes a polymer matrix. For example, a carbon nanofiber-polyurethane (CN:PU) or a polyurethane-carbon nanofiber (PU:CN) is a nanocomposite. The term "nanocomposite" generally refers to a composite polymer material comprising at least a plurality of nanoparticles disposed in any suitable manner on the composite material. The composite may also be referred as a matrix or a polymer substrate or generally a substrate. The carbon nanofibers as used herein refer to single walled nanotubes (SWNT), double wall nanotubes (DWNT) or multiwalled nanotubes.

Neural and orthopedic prostheses or implants include devices and probes for monitoring, catheters and implants for drug delivery, loops, guide wires, valves, artificial vessels, neural bridges, shunts, and stents for cell repair and maintenance, and other prostheses that are used for continuous monitoring and treatment of affected tissue. An exemplary silicon electrode probe for neural applications is disclosed in Hetke et al., (2003), the disclosure of which is incorporated herein by reference (Hetke, J. F. and Anderson, D. J., "Silicon electrodes for extracellular recording," In: Handbook of Neuroprosthetic Methods, (Finn and LoPresti, eds.), CRC Press LLC, pp. 163-191, 2003). Fabrication methods for probes used in neural applications is described by Najafi, K (1997) in Najafi, K. "Micromachined systems for neurophysiological applications.", Handbook of microlithography, micromachining, and microfabrication, Volume II: Micromachining and Microfabrication, SPIE, 1997, the disclosure of which is hereby incorporated by reference. Other publications that discuss fabrication methodologies for neural prostheses include Neuman et al., Fabricating Biomedical Sensors with Thin-Film Technology, IEEE EMB Mag. 13: 409-419, 1994 and Wise et al., Microfabrication Techniques for Integrated Sensors and Microsystems. Science 254: 1335-1342, 1991.

U.S. Pat. No. 5,698,175 relates to a process for purifying, uncapping and chemically modifying carbon nanotubes, and more particularly to a process for easily obtaining highly purified nanotubes for use in the field of chemistry, drugs and electronics, the disclosure of which is hereby incorporated by reference.

U.S. Pat. No. 6,063,243 relates generally to nanotube fabrication and more specifically to manufacture of nanotubes containing boron, carbon and nitrogen, the disclosure of which is hereby incorporated by reference. U.S. Pat. No. 5,365,073 relates to a nanofabricated electroconductive structure and a method of fabrication thereof using a probe for use in a scanning tunneling microscope (STM), the disclosure of which is hereby incorporated by reference.

There are structural similarities between the nanomaterials and the components of some of the biological organs, particularly the bone and the neural system at the topographical level. For example, living systems are governed by molecular behavior at nanometer scales. For both the orthopedic and neural implants, surface properties determine the interact of the implants with the surrounding cells that are in contact with the biomaterial surfaces after implantation. Topography of biological molecules such as proteins, in tissue types, is a factor in designing suitable nanomaterials.

The molecular building blocks of life—proteins, nucleic acids, lipids, carbohydrates, proteins, and the like—are examples of materials that possess unique properties determined by their size, folding, and patterns at the nanoscale. For example, with respect to bone, hydroxyapatite (the major inorganic component of bone) is between 2 and 5 nm in width and 50 nm in length, while type I collagen (the major organic component of bone) is a triple helix 300 nm in length and 0.5 nm in width, and has a periodicity of 67 nm. For neural tissue, laminin is a key extracellular matrix component that has a cruciform configuration of approximately 70 nm in width and length. The structural dimensions of biological molecules is in contrast to the surfaces provided by traditional implants which have constituent micron grain or particles sizes that provide topographies that do not resemble biological surfaces.

Silicon, a standard material that has been used as neural probes tends to induce significant glial scar tissue formation. This gliotic response is mediated largely by astrocytes and forms at implant and injury sites. Gliotic scar tissue is a common difficulty in the field of neural prosthetics and cause impairment of implant functionality, especially with chronic implant applications. The formation of gliotic scar tissue results in increased electrode impedance around the implant, decreased local density of neurons, and reduced axonal regeneration.

Physiological surfaces such as extracellular matrices that cells normally interact with are composed of proteins with nanoscale surface dimensions. We designed synthetic materials using nanofibers to mimic the properties of natural tissues as part of a method to minimize reactions such as, for example, the foreign body response and scar tissue formation.

In an embodiment, an exemplary neural or orthopedic implant includes a polyurethane (PU)-carbon nanofiber (CN) composite forming a part of or over its surface. The composite has the nanomaterial in the range of about 2 to 500 nm, wherein the carbon nanofibers is in a range of about 2% to 100% by weight and the composite polyurethane is in a range of about 98% to 0% by weight.

In an embodiment, an exemplary neural or orthopedic implant includes a nanomaterial forming a part of or over the implant's surface, wherein the nanomaterial is in the range of about 2 to 200 nm.

In an embodiment, an exemplary neural or orthopedic implant includes a nanomaterial forming a part of or over the implant's surface, wherein the nanomaterial is in the range of about 10 to 100 nm.

In an embodiment, the carbon nanofibers are aligned in a particular orientation to promote axonal or neuronal growth. In an embodiment, the carbon nanofibers are functionalized, for example, with an agent such as 4-hydroxynonenal.

In an embodiment, an exemplary neural or orthopedic implant includes a polyurethane (PU)-carbon nanofiber (CN) composite forming a part of or over the implant's surface. The composite has the nanomaterial in the range of about 10 to 100 nm and with a load density of about 80:20 (wt % CN:PU).

In an embodiment, an exemplary neural or orthopedic implant includes a polyurethane (PU)-carbon nanofiber (CN) composite forming a part of or over the implant's surface, wherein the composite has a nanomaterial in the range of about 10 to 100 nm and with a load density of about 90:10 (wt % CN:PU).

In an embodiment, an exemplary neural or orthopedic implant includes a polyurethane (PU)-carbon nanofiber (CN) composite forming a part of or over the implant's surface, wherein the composite has a nanomaterial in the range of about 10 to 100 nm and with a load density of about 90:10 (wt % CN:PU).

In an embodiment, an exemplary neural or orthopedic implant includes a polyurethane (PU)-carbon nanofiber (CN) composite forming a part of or over the implant's surface, wherein the composite comprises substantially of a nanomaterial in the range of about 10 to 100 nm.

The nanomaterial can be coated over the entire device or to a portion of the device by dipcoating, spraying, molding, or by any other suitable method. The device can also be formed from the nanomaterial. The composite nanomaterial can also be layered or glued on the device.

A neural implant coated with or made from a suitable nanomaterial of the present disclosure would be secured in the neurological tissue using known techniques to minimize scar formation. The nanomaterial in the implant may also be aligned to guide axonal growth if necessary. The nanomaterial may also be functionalized to promote better bonding with the surrounding tissue. The implant may also provide neuronal stimulants such as, for example, nerve growth factors, to promote neuronal growth. A neural implant can be a neural probe for prolonged monitoring, diagnosis, and treatment of neurological disorders.

An orthopedic implant coated with or made from a suitable nanomaterial of the present disclosure would be secured in a desired tissue using known techniques to minimize fibroblast encapsulation.

The composite nanomaterials were constructed using carbon nanofibers and a polycarbonate urethane matrix (PU or PCU). The carbon fibers used, were selected from multi-walled carbon fibers with four different diameters (from 60 to 200 nm). They were synthesized using catalytic and chemical vapor deposition methods and were acquired from Applied Sciences, Inc./Pyrograf Products, Inc. (Cedarville, Ohio). The fibers were separated into two groups—conventional (with diameters greater than 1.00 nm, specifically 125 and 200 nm), and nanophase (with diameters of 100 nm or less, specifically 60 and 100 m). A high surface energy (125-140 $mJ/m^2$) and low surface energy (25-50 $mJ/m^2$) fiber was represented in each group. The low surface energy fiber was left as grown, and the high surface energy fiber was obtained by pyrolytic stripping of the carbon fiber to remove the outer hydrocarbon layer. Each type of carbon fiber was uniaxially pressed using a steel-tool die at 4000 psi for 3 minutes at room temperature to obtain a disc (1.327 $cm^2$ surface area) for cytocompatibility studies. The discs were then exposed to ultraviolet radiation for sterilization for 15 min.

The PU used was an FDA-approved polycarbonate urethane (PU or Carbothane, catalogue no PC-3575A, Thermedics) matrix with a specific weight of 1.15 g $cm^{-3}$ was used as the substrate. PU was chosen because PU is a thermoelastic elastomer, with good mechanical (ultimate elongation 470%) and oxidative stability properties, but is non-conductive as described in Thapa et al., (2003).

Other matrix or polymer composite materials include, for example, polymers such as polyurethanes, polyvinyls, polyesters, polyacyrlates, polymethacrylates, copolymers thereof or any other thermostable, biocompatible matrix material that interacts compatibly with the nanoparticles and the surrounding tissue.

Composites were formed from carbon fibers and polycarbonate urethane (PU) matrix in different proportions. Compositions with varied polycarbonate urethane (Thermedics Polymer Products; PC3575A) to carbon nanofiber (CN) weight percents were used (PU:CN-100:0, 98:2, 90:10, 75:25). Polycarbonate pellets were allowed to dissolve in chloroform for 1 hour, while the carbon nanofibers were sonicated in chloroform for 1 hour, and then the two solutions were mixed. This mixture was then sonicated for 1 hour, poured into Teflon petri dishes, and cured in a vacuum overnight. Discs (with a surface area of 1.327 $cm^2$) were cut from the polymer for cell adhesion experiments. All material sample (discs) (except the monolithic control CNs with 0 and 100% CN by weight) were also separately degreased and sonicated in acetone and ethanol for 10 min according to Thapa et al., (2003). All samples (discs) were exposed to ultraviolet light for 15 min on each side for sterilization purposes prior to experiments with cells. Borosilicate glass coverslips (Fisher Scientific) were used as reference substrates. The coverslips were degreased and sonicated sequentially with acetone and ethanol and were then etched with 1 N NaOH. Autoclaving was used for sterilization.

The nanomaterials and or the matrix materials can be functionalized to enhance interaction between the matrix material and also the biological surroundings. Functionalization of nanomaterials can be achieved with organic and inorganic agents. One such functionalization agent is 4-hydroxynonenal.

The composite materials' effectiveness for reducing the glial scar response was tested by way of an adhesion, proliferation, phosphatase activity, and protein content assays with astrocytes. These assays are described in detail in the Materials and Methods section of this disclosure.

Figure 4:
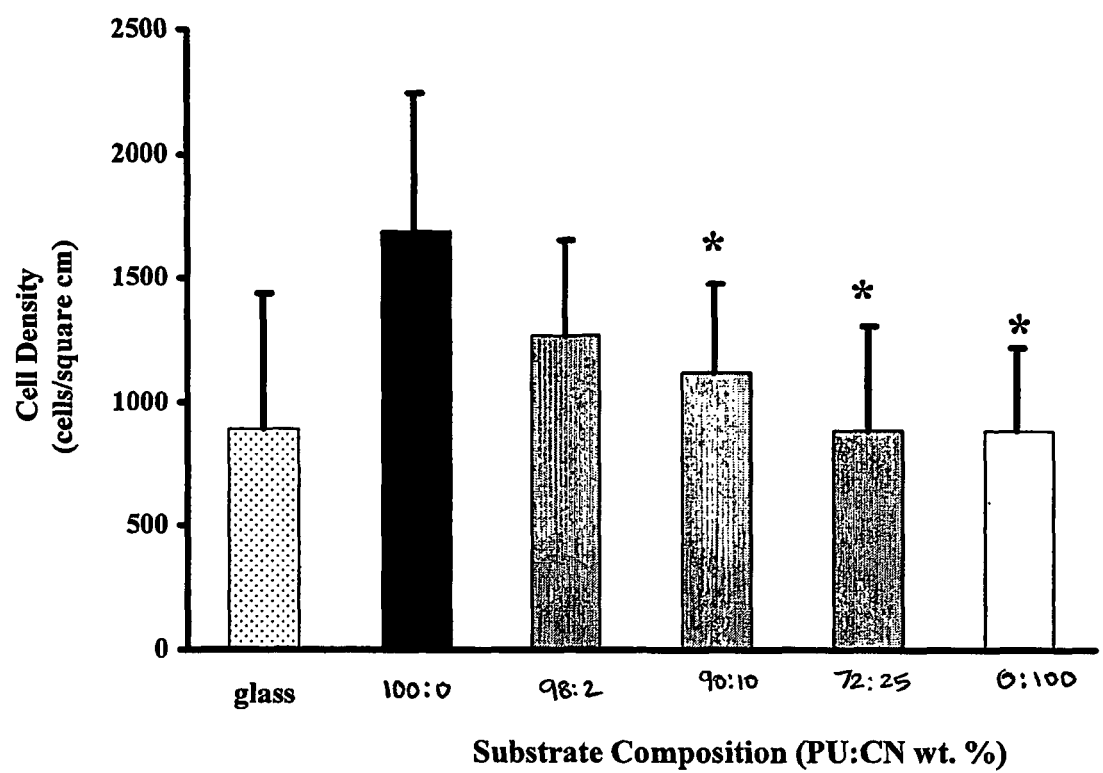
FIG. 4 shows decreased astrocyte cell adhesion density with increased numbers of CNs in PU. Values are mean +/−SEM; n=3; .p<0.1 compared to 100:0 PU:CN wt %.

Adhesion of astrocytes and proliferation on various composite nanomaterials were decreased in vitro. Decreased adhesion of astrocytes leads to reduced glial scar tissue formation in vivo. Astrocyte adhesion was decreased with increasing numbers of CNs in a PU matrix (FIG. 4). Although the number of astrocytes was statistically similar between 100:0 and 98:2 PU:CN wt %, significantly $p<0.1$) fewer astrocytes adhered on 90:10, 75:25, and 0:100 PU:CN wt % compared to 100:0 PU:CN wt %. The smallest number of astrocytes adhered on 75:25 and 0:100 PU:CN wt % formulations; about half as many astrocytes adhered on these formulations as on 100:0 PU:CN wt %. Since prolonged extensive functions of astrocytes lead to unwanted glial scar-tissue formation, these data demonstrate that increased numbers of CNs in a PU matrix minimize glial scar-tissue formation that limits neural implant device functionality. Cell culture data strongly indicates that some or all parts (both non-conductive and conductive) of a neural prosthetic device could be fabricated by altering the amount of CN content in PU while still maintaining the ability to limit astrocyte function and promote neuron function. An optimal balance of CN:PU may be achieved such that both neuron extension and decreased astrocyte adhesion is enabled. For example, a CN:PU ratio of 90:10% is an embodiment.

Astrocytes (glial scar tissue-forming cells) were seeded onto various substrates for adhesion, proliferation, and long-term function studies (such as total intracellular protein and alkaline phosphatase activity). Results indicated that astrocytes preferentially adhered and proliferated on carbon fibers that had the largest diameter and the lowest surface energy. Composite substrates were formed using different weight percentages (0-25 wt. %) of the nanophase, high surface energy fibers in a polycarbonate urethane matrix. Results indicated decreased adhesion of astrocytes with increasing weight percents of the high surface energy carbon nanofibers in the polymer composite; this further demonstrates that formulations containing carbon fibers in the nanometer regime limit astrocyte functions leading to decreased glial scar tissue formation. Positive interactions with neurons, and, at the same time, limited astrocyte functions leading to decreased gliotic scar tissue formation are required for increased neuronal implant efficacy.

Figure 7:
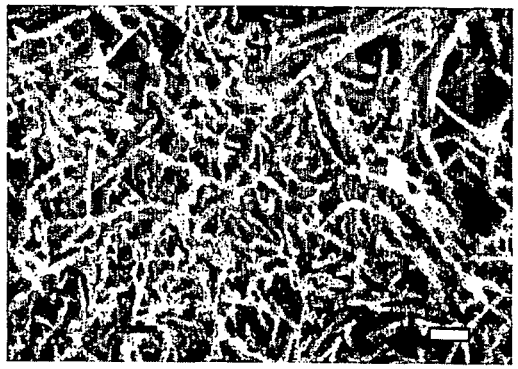
FIG. 7 shows high magnification scanning electron micrographs of the following carbon fiber discs: (a) conventional fiber with low surface energy, (b) conventional fiber with high surface energy, (c) nanophase fiber with low surface energy, and (d) nanophase fiber with high surface energy. Original magnification=10,000×; 5 kV; bar=1 micron.
Figure 7:
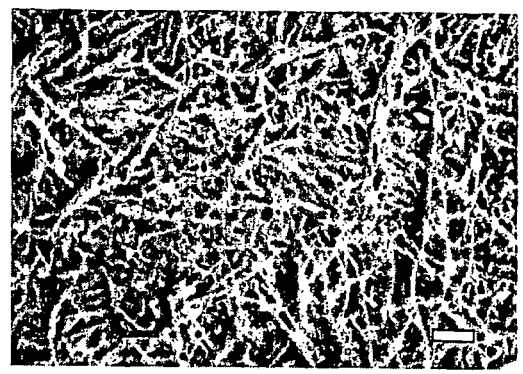
Figure 7:
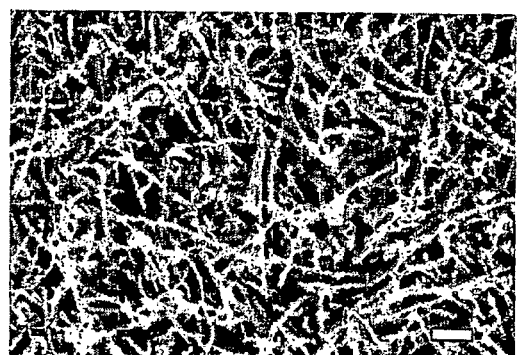
Figure 8:
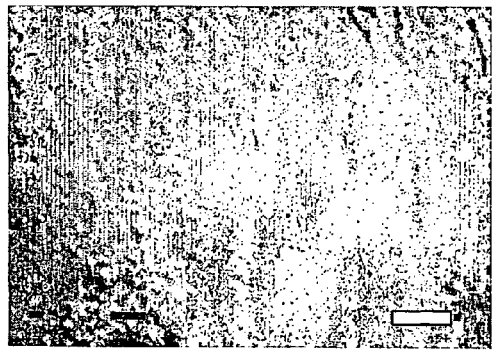
FIG. 8 shows a high magnification scanning electron micrographs of varying compositions (by weight) of polycarbonate urethane (PCU) and 60 nm carbon nanophase fibers (CN) with high surface energy: (a) 100:0 (PCU:CN), (b) 98:2, (c) 90:10, and (d) 75:25. Original magnification=(a) 15,000×; (b)-(d) 10,000×; 5 kV; bar=1 micron.
Figure 8:
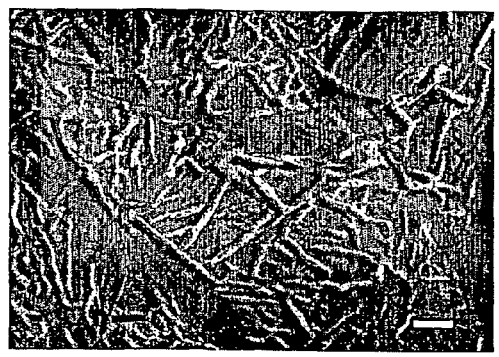
Figure 8:
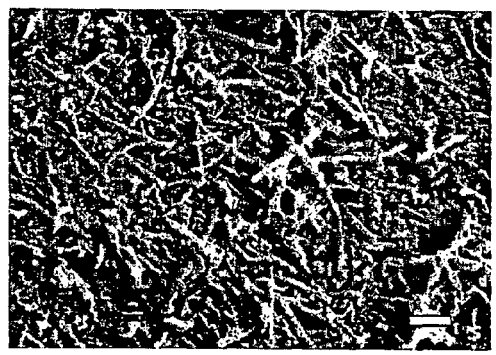
Figure 8:
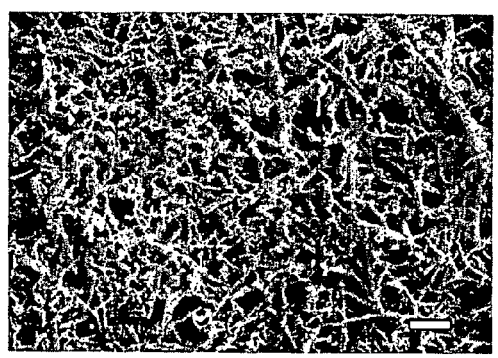
Figure 9:
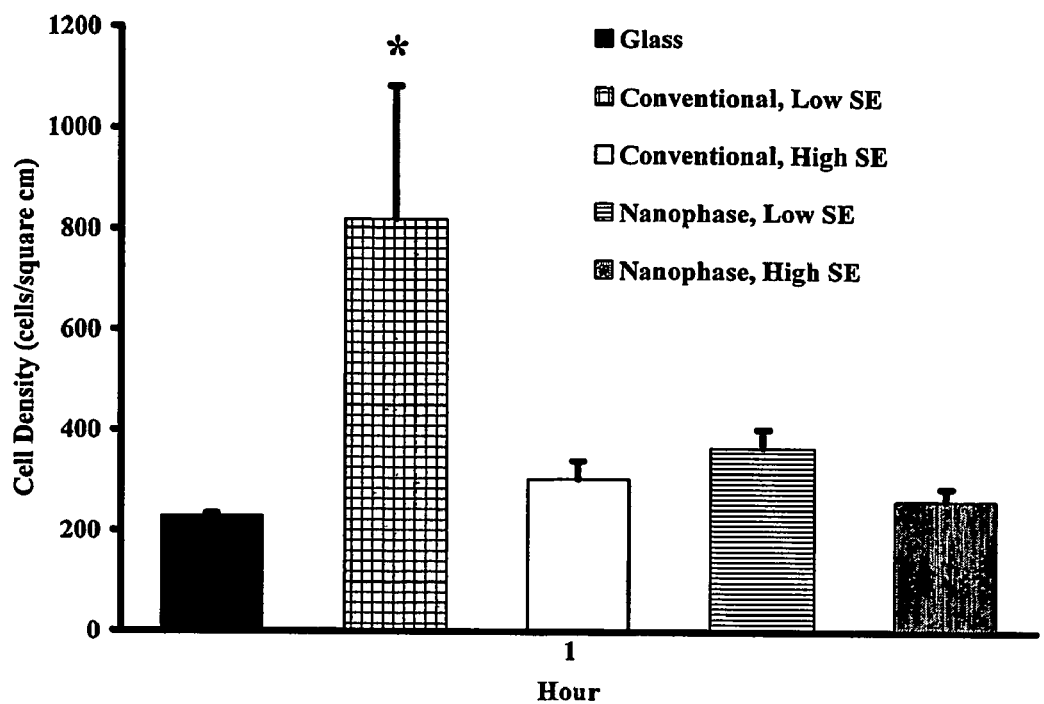
FIG. 9 shows astrocyte adhesion on low and high energy surfaces: borosilicate glass (reference substrate), conventional fibers (200 nm) with low surface energy (SE), conventional fibers (125 nm) with high surface energy, nanophase fibers (100 nm) with low surface energy, and nanophase fibers (60 nm) with high surface energy; all under standard cell culture conditions for 1 hour. Values are mean±SEM; n=3; * p<0.1 (compared to respective nanophase fiber with similar surface energy).

Scanning electron micrographs at high magnification provided evidence of the varying fiber diameters (FIG. 7). The scanning electron micrographs for the composites of polycarbonate urethane and 60 nm carbon fibers revealed increasing fiber composition per increasing weight percent of carbon (FIG. 8). The fibers caused an increased surface roughness in the 75:25 weight percent (PCU:CN) composite. Electron spectroscopy for chemical analyses confirmed that the disc surfaces were composed primarily of carbon (TABLE 3). The results indicated the presence of small amounts of oxygen on the discs, although less was found on the high surface energy (125-140 $mJ/m^2$) fiber discs than on the low surface energy (25-50 $mJ/m^2$) discs (2.5±0.6 to 3.0±0.2% compared to 1.0±0.2 to 1.7±0.5%). The high surface energy conventional and nanophase carbon fiber discs did show a slight sulfur contamination of 0.4±0.1 to 0.5±0.1%, respectively.

The resistivity of the composites decreased exponentially as the weight percent of carbon nanofibers in PCU composites increased (TABLE 2). These values ranged from 20,500 Ωm for the 98:2 (PCU:CN wt. %) composite to 0.354 Ωm for the 75:25 composite. This wide range of values indicates great flexibility in design of electrical properties for these materials by just varying the weight percentage of carbon nanofibers.

Figure 10:
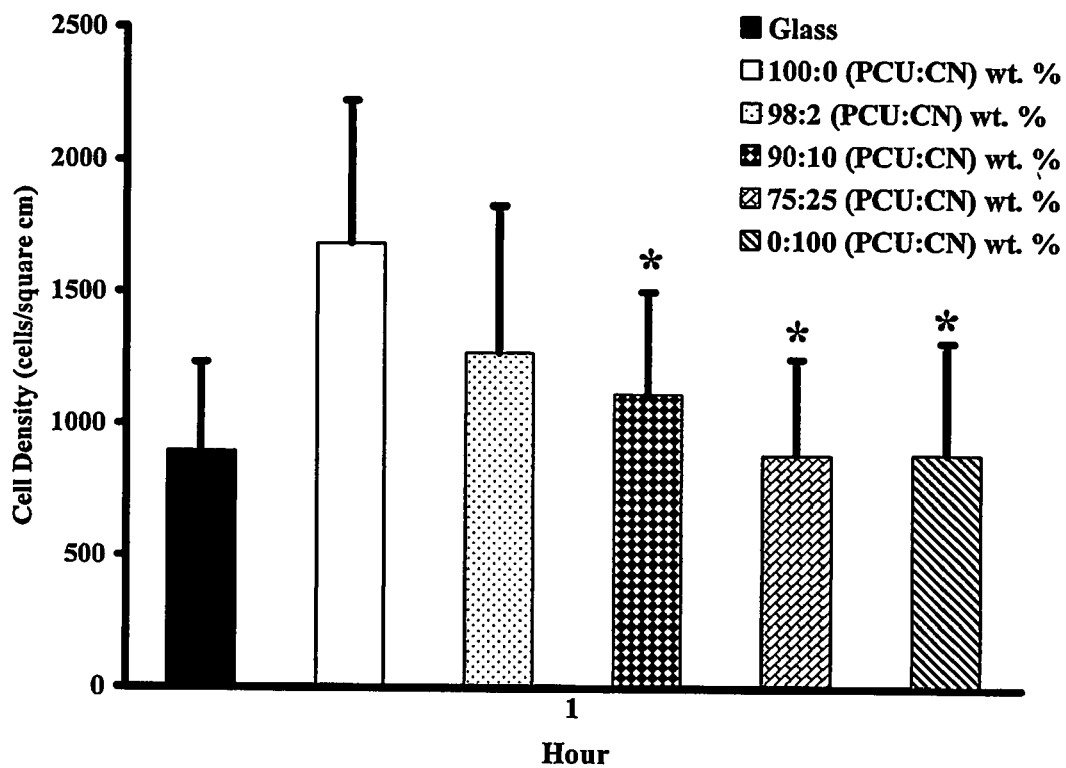
FIG. 10 shows astrocyte adhesion cultured on the following substrates: borosilicate glass (reference substrate), compositions (by weight) of polycarbonate urethane (PCCU) and carbon nanophase fiber (CN; 60 nm with high surface energy) PCU:CN substrates: 100:0, 98:2, 90:10, 75:25, and 0:100; all under standard cell culture conditions for 1 hour. Values are mean±SEM; n=3; * p<0.1 (compared to 100:0 PCU:CN wt. %).

After one hour, astrocytes had preferentially adhered to the low surface energy, conventionally sized carbon fiber disc (FIG. 10). This result was significantly ($p<0.1$) greater at 123% higher cell density than adhesion to the nanophase fiber with similar surface energy. The number of astrocytes that adhered to high surface energy fibers of both the nanophase and conventional size regimes was similar.

Adhesion to the pure polycarbonate urethane was greater than to most of the composites containing the 60 nm carbon fiber (FIG. 10). In other words, substrate compositions of 90:10 and 75:25 (PCU:CN by wt. %) had significantly less ($p<0.1$) adherent cells when compared to polycarbonate urethane (100:0). The differences in adhesion between the 98:2, 90:10, 75:25, and 0:100 composites were not statistically significant.

Figure 11:
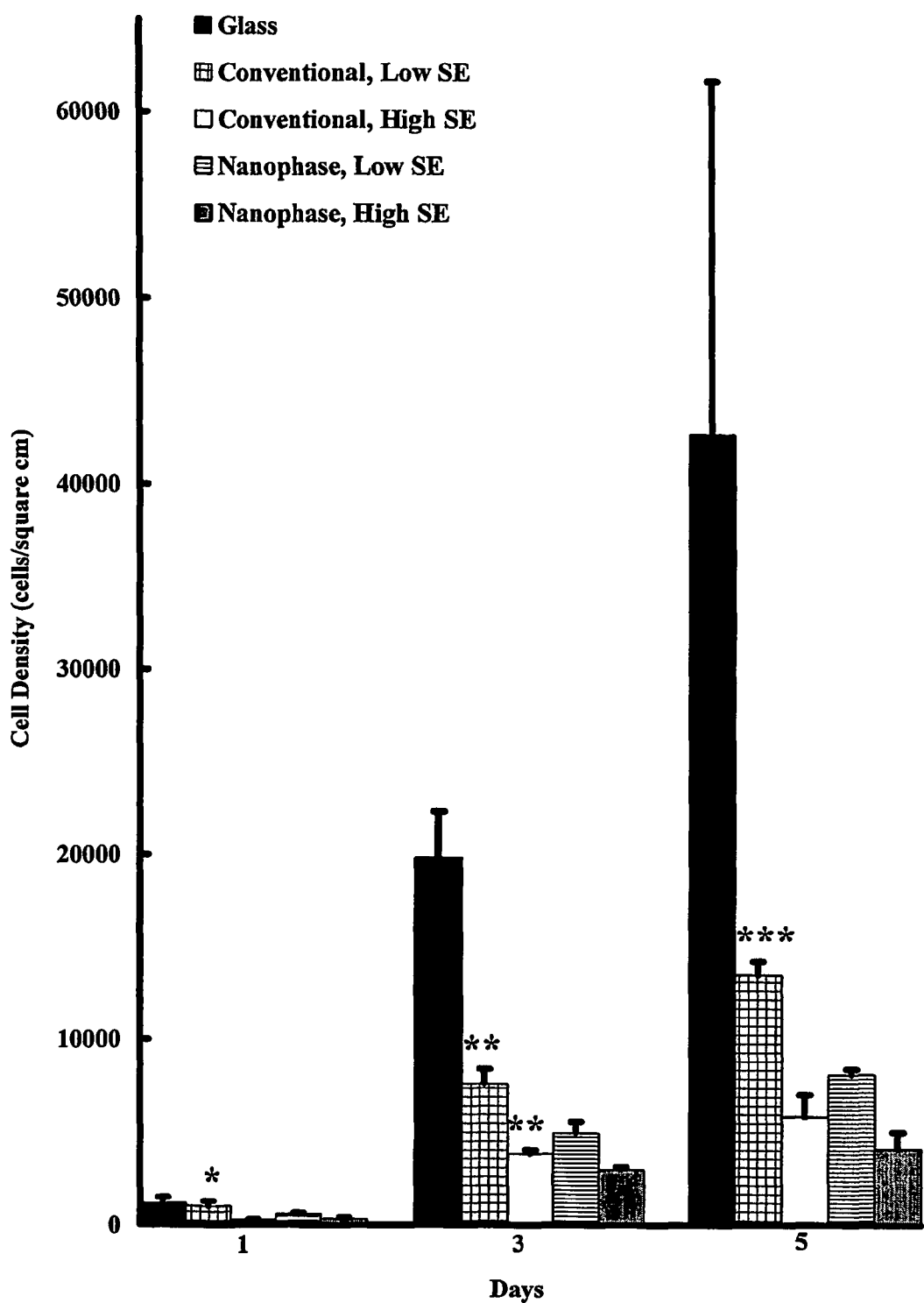
FIG. 11 shows astrocyte proliferation cultured on the following substrates: borosilicate glass (reference substrate), conventional fibers (200 nm) with low surface energy (SE), conventional fibers (125 nm) with high surface energy, nanophase fibers (100 nm) with low surface energy, and nanophase fibers (60 nm) with high surface energy. Astrocytes were cultured under standard cell culture conditions for 1, 3, and 5 days. Values are mean±SEM; n=3; * p<0.1,  p<0.05, * p<0.01 (compared to respective nanophase fiber with similar surface energy).

At the 1, 3, and 5 day time points, the cell density was greater on the low surface energy conventional carbon fiber disc, than on the low surface energy nanophase substrate (FIG. 11). This result was significant at each time point ($p<0.1$ at one day, $p<0.05$ at 3 days, and $p<0.01$ at 5 days), and was up to 66% greater cell density at 5 days. Compared to the nanophase high surface energy fiber, the conventional high surface energy fiber had significantly more cells after 3 days ($p<0.05$); more cells were on the conventional high surface energy fiber after 5 days, but this was not statistically different from nanophase high surface energy fibers.

Figure 12:
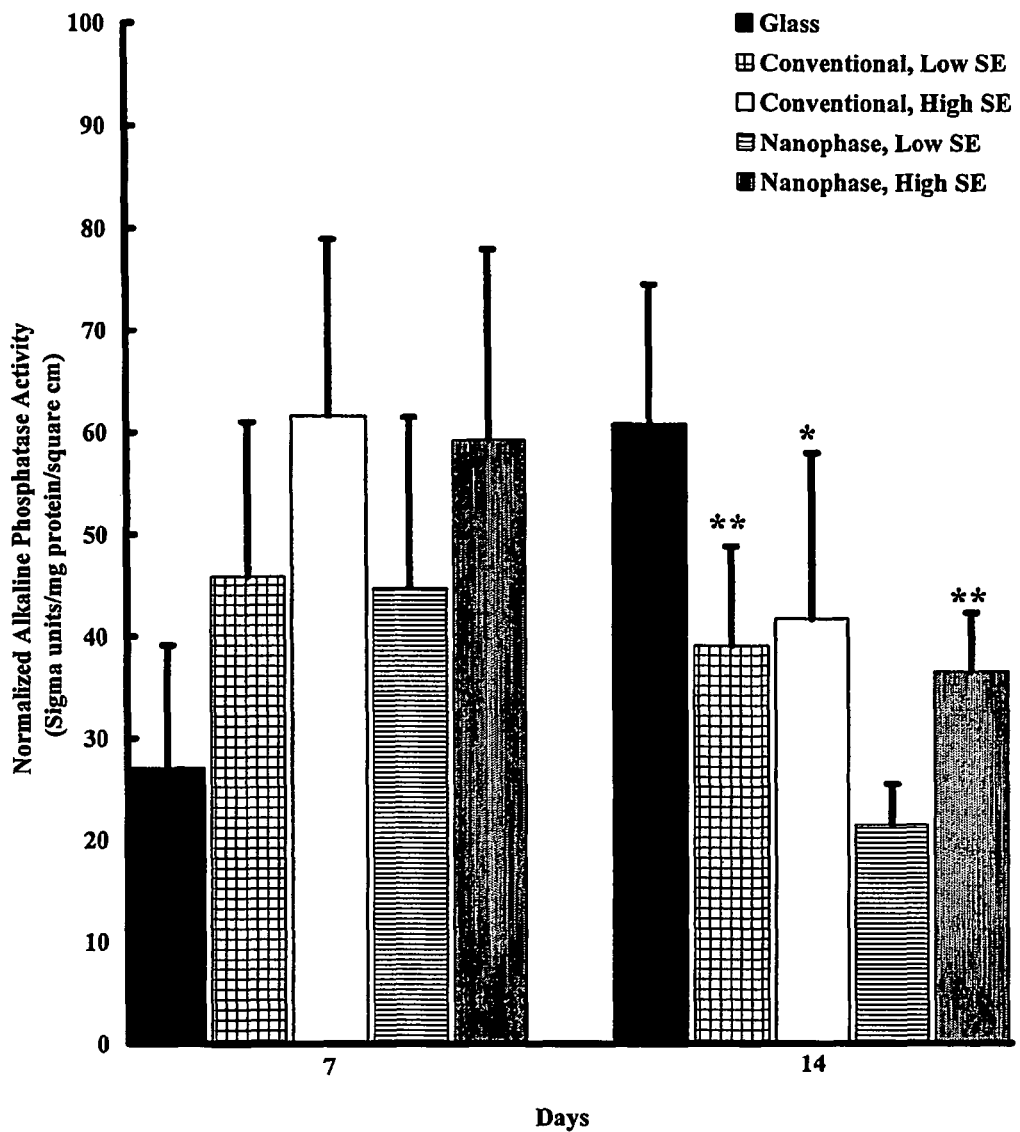
FIG. 12 shows normalized astrocyte alkaline phosphatase activity cultured on the following substrates: borosilicate glass (reference substrate), conventional fibers (200 nm) with low surface energy (SE), conventional fibers (125 nm) with high surface energy, nanophase fibers (100 nm) with low surface energy, and nanophase fibers (60 nm) with high surface energy. Intracellular alkaline phosphatase activity (Sigma units/mg protein/square cm) was determined after 7 and 14 days. Values are mean±SEM; n=3; * p<0.13, ** p<0.08 (compared to low surface energy nanophase fiber).

The alkaline phosphatase activity assay was normalized by dividing respective values of the total intracellular protein content and the substrate surface area. At 7 days, there was not a significant difference in alkaline phosphatase production between the astrocyte cells cultured on the four different carbon fibers (FIG. 12). Alkaline phosphatase production was significantly reduced at 14 days on the low surface energy, nanophase fiber when compared to the other three types of fibers ($p<0.13$ for the conventional high surface energy fiber; and $p<0.08$ for the conventional low surface energy and nanophase high surface energy fibers). Compared to all other carbon fibers, this result revealed 70 to 93% less of this enzyme produced on the low surface energy carbon nanofiber.

Astrocytes exhibited significantly increased cell density on low surface energy and conventionally sized (with a diameter greater than 100 nm) carbon fibers at 1 hour and 1, 3, and 5 day time periods. Nanofibers minimized astrocyte interactions. Alkaline phosphatase production indicated that nanophase fibers reduced astrocytic activity even after prolonged time periods of 14 days.

A 60 nm high surface energy carbon nanofiber was used for further investigation. Matrix modifications of carbon nanofibers enhances bulk mechanical and electrical properties. Polycarbonate urethane (PCU) was used as an exemplary matrix polymer based on its proven clinical applications. The carbon nanofibers were combined with polycarbonate urethane to obtain nanoscale carbon fibers in a polymer matrix having desirblae mechanical properties. The compositions tested (90:10, 75:25; PCU:CN wt. %) had significantly less adhesion of astrocytes than the pure polymer. Nanophase carbon fibers decreased astrocyte adhesion in a polymer matrix by creating a surface with a high degree of biologically inspired nanometer roughness. Furthermore, the 75:25 composition had similar adhesion to the pure carbon nanofiber disc, and the electrical resistivity of this composite was also similar to the pure carbon nanofiber disc (0.354 compared to 0.0598 Ωm, respectively). Thus, the benefits of using PCU with carbon nanofibers is realized with the flexibility of a range of electrical properties (such as conductivity) available for designing materials important for neural applications. Astrocyte function was minimized on carbon nanofibers.

Figure 5:
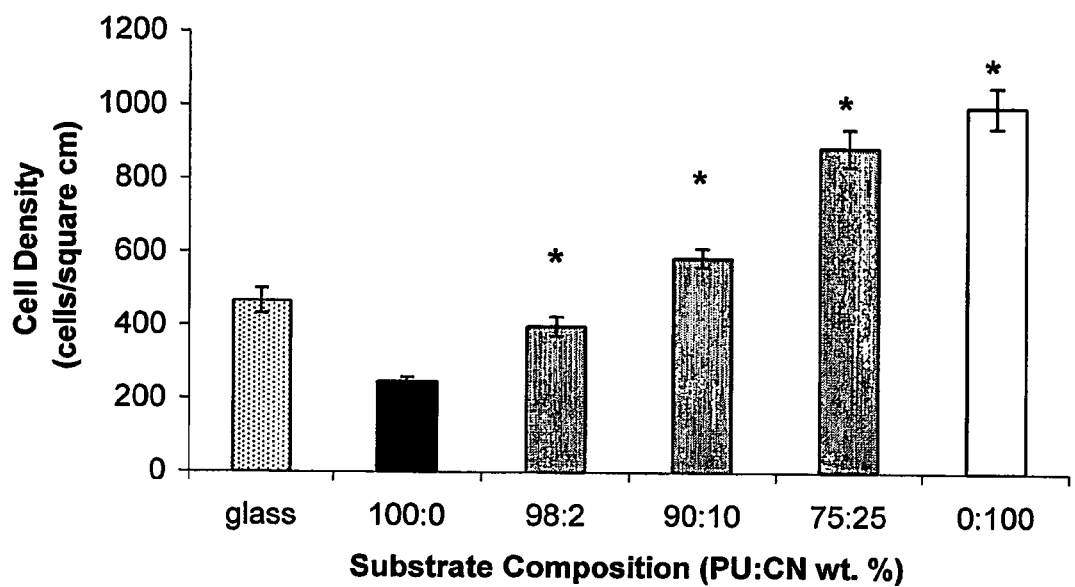
FIG. 5 shows increased osteoblast cell adhesion density with increased numbers of CNs in PU. Values are mean +/−SEM; n=3; .p<0.1 compared to 100:0 PU:CN wt %.

Interactions of osteoblasts was enhanced and adhesion of fibroblasts was decreased with nanomaterials. Adhesion of osteoblasts increased with increasing weight fractions of CNs in PU (FIG. 5). With only a 2 wt % increase of CNs in the PU matrix, significantly ED<0.1) more osteoblasts adhered. Up to three and four times the number of osteoblasts that adhered on 100:0 PU:CN wt % adhered on 90:10 and 75:25 PU:CN wt % composites, respectively. Statistically similar numbers of osteoblasts adhered on 75:25 compared to 0:100 PU:CN wt % formulations.

Figure 6:
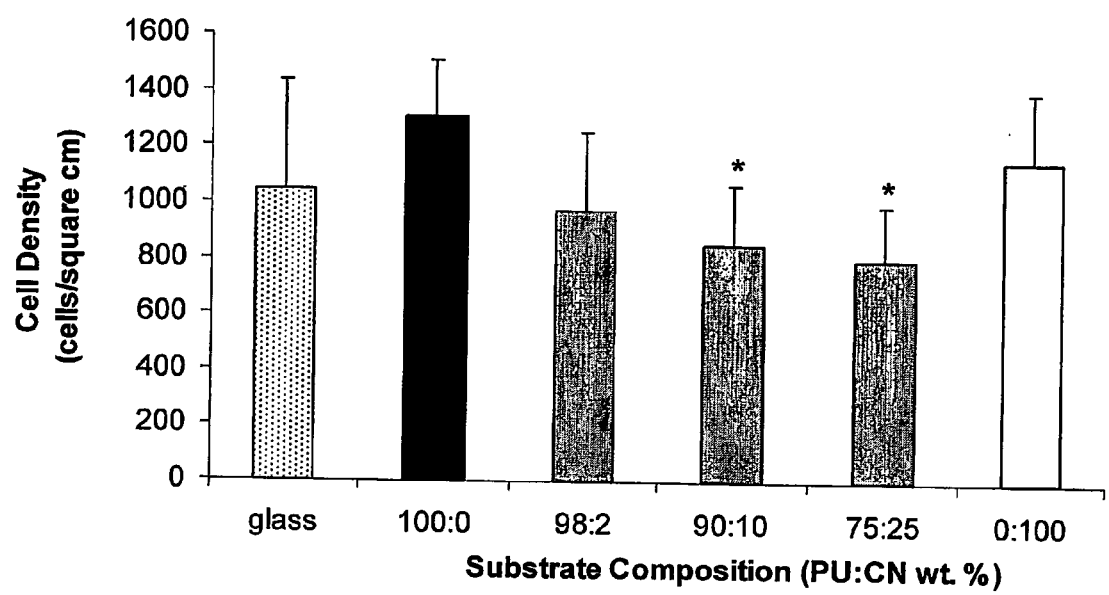
FIG. 6 shows decreased fibroblast cell adhesion density with increased numbers of CNs in PU. Values are mean +/−SEM; n=3; .p<0.1 compared to 100:0 PU:CN wt %.

Adhesion of fibroblasts was decreased on PU composites with increasing numbers of CNs (FIG. 6). Similar numbers of fibroblasts were measured on 100:0 and 98:2 PU:CN wt %; however, the number of adherent fibroblasts significantly decreased with 10 and 25 wt % of CNs compared to 100 wt % PU. Prolonged functions of fibroblasts at the implant interface limits necessary osseointegration events and results in callus formation that may lead to implant loosening and eventual failure. Materials (such as the CNs in a PU matrix that this study demonstrated) which increase functions of osteoblasts while at the same time decreasing functions of fibroblasts have the potential to effectively bond to juxtaposed bone. Based on the mechanical and cell culture data, CNs in a PU matrix is considered for both loading (as a coating material) and non-loading orthopedic applications while still maintaining the ability to limit fibroblast and promote osteoblast function. Nanophase materials have increased numbers of atoms at the surface, greater numbers of material defects (such as grain boundaries) at the surface, and increased electron delocalization at the surface: properties that will certainly alter surface energetics of a composite containing nanophase compared to conventional materials. Such altered surface energetics of nanophase materials have changed interactions of proteins that influence subsequent cellular adhesion. For example, the conformation of adsorbed vitronectin, a linear protein of 15 nm in length contained in serum that mediates osteoblast adhesion is different on nanophase compared to conventional grain size ceramics. Compared to conventional ceramics, nanophase ceramics promoted unfolding of vitronectin to expose cell-adhesive epitopes (such as arginine-glycine-aspartic acid, RGD) recognized by specific osteoblast-membrane receptors. Similar altered protein interactions important for cell function may be occurring on the novel composites in the present disclosure.

Interactions of neurons with polymer materials containing carbon nanotubes (CN) were increased. PC-12 cells were seeded onto substrates coated with laminin (5 µg ml$^{-1}$; Sigma) at 13 500 cells cm$^{-2}$ and allowed to differentiate for 3 d. At the end of the time period, the cells were rinsed with PBS, fixed with formaldehyde and stained with DiI (D-282; Molecular Probes). The number of neurites (extensions that may form axons) were determined per cell after three days as a measure of favorability to the materials of interest. Cell counts were expressed as the average number of cells in five random fields per square centimeter of substrate surface area. The number of neurites per neuron was determined for each neuron in five random fields per substrate.

Figure 2:
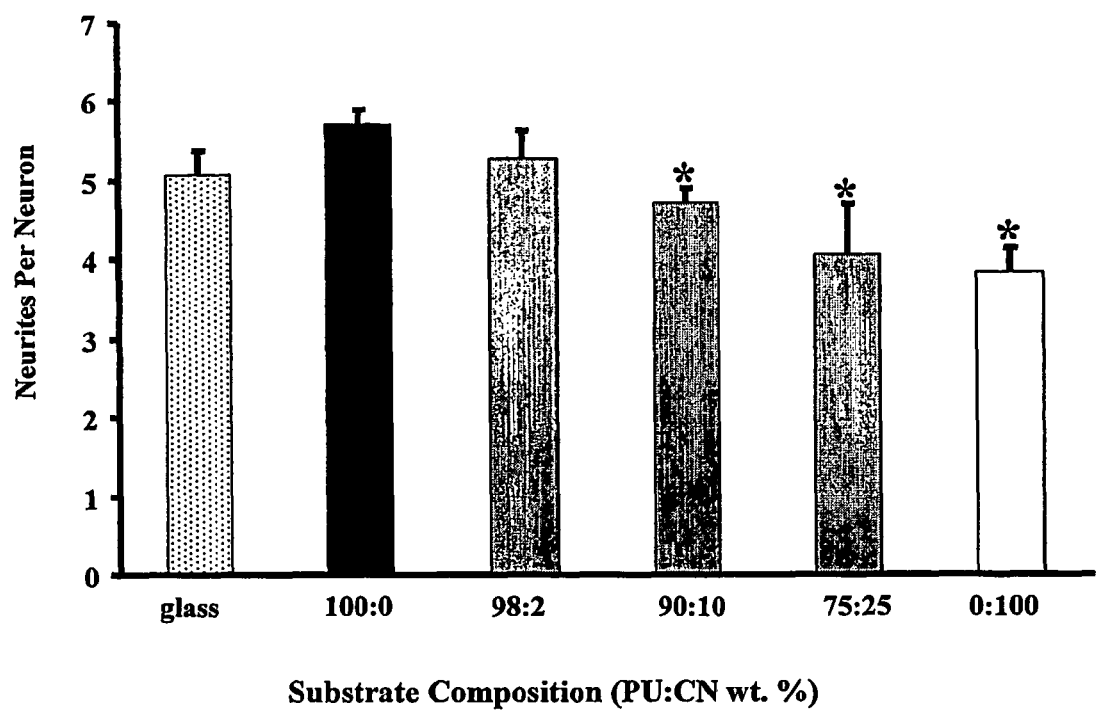
FIG. 2 shows an optimal neurite extension for neurons cultured on all PU:CN materials. Time=3 d. Values are mean +/−SEM; n=3; .p<0.1 compared to 100:0 PU:CN wt % matrix.
Figure 3:
FIG. 3 illustrates the representative images of optimal neurite extension for neurons cultured on all PU:CN materials. Scale bar=10 μm; scale bar=20 μm.
Figure 3:
Figure 3:
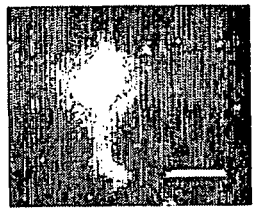
Figure 3:
Figure 3:
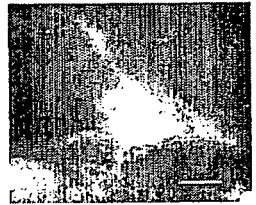

First evidence of neurite extension from neurons cultured on 100:0 and 98:2 PU:CN wt % formulations are shown in FIG. 2 and FIG. 3. However, there was a slight decrease in the extension of neurites in neurons cultured on composites containing more than 10 wt % CNs and on 100 wt % CNs. Although this decrease was statistically significant (p<0.1), it is important to note that, between all substrates, the difference in the number of neurites extended per neuron was only on average approximately 1.6 (from 5.6 to 4.0 neurites extended per neuron on the 100:0 and 0:100 PU:CN wt %, respectively). Since a neurite must extend from a neuron before it becomes an axon, these results show the ability of PU:CN formulations to promote interactions with neurons needed for successful neural probes.

Figure 13:
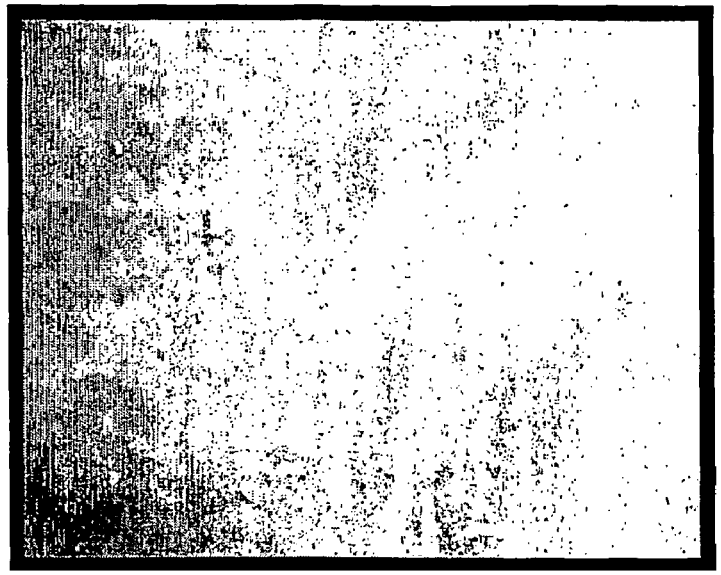
FIG. 13 shows an alignment of carbon nanofibers for neural applications. Arrow indicates alignment.
Figure 13:
Figure 13:
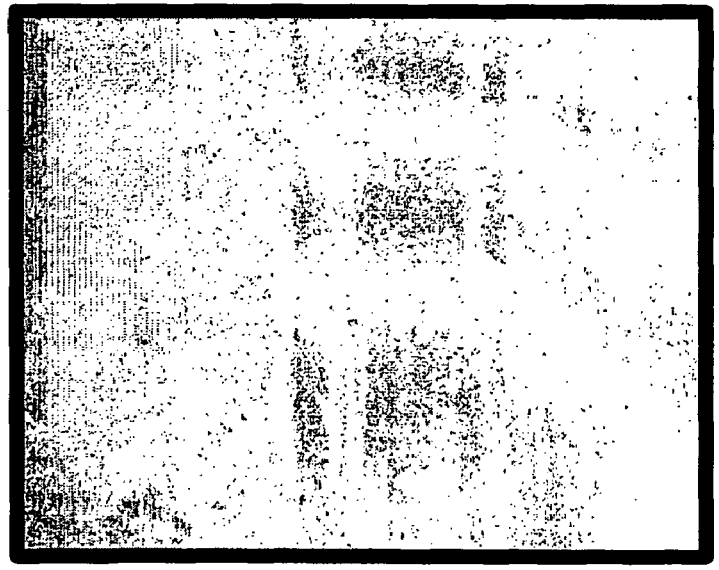

Aligned carbon nanofibers in a polymer matrix is shown in FIG. 13. Random agglomerated carbon nanofibers in the polymer matrix before the application of the electric field becomes aligned in the presence of an electric field. Aligned carbon nanofibers in the polymer matrix in the presence of an electrical field is observed (FIG. 13). By controlling the alignment of carbon nanofibers in a polymer matrix, the ability to control axon extension in neurons and control of scar tissue is achieved.

The above indicates that a neural implant coated with or made from a suitable nanomaterial of the present disclosure could be secured in the neurological tissue using known techniques. The nanomaterial in the implant would also be aligned (as in FIG. 13) to guide axonal growth and reduce scar tissue formation.

Multiwalled carbon nanofibers (CN), synthesized using catalytic and chemical vapor deposition, were acquired from Applied Sciences, Inc./Pyrograf Products, Inc. Composites were formed from 100 nm, low surface energy fibers (25-50 mJ/m2) or 60 nm, high surface energy fibers (125-140 mJ/m2) and poly carbonate urethane (Thermedics Polymer Products, PC3575A). Polycarbonate urethane pellets were allowed to dissolve in chloroform at 25° C. for 40 min with sonication, then carbon nanofibers were added and sonication continued for another hour. This mixture, when viscous, was poured into wells of a microscope slide fashioned with parallel copper plate electrodes. Voltage was applied to the solution to create a homogeneous electric field. Voltages up to 700 were applied to the wells until the composite had cured.

Characterization of surface roughness: Various formulations of carbon nanotubes (CN) at the surface of the polyurethane (VU) matrix were fabricated (from concentrations of 100:0 to 0:100 PU:CN wt %) of added CNs (FIG. 1). Larger numbers of CNs in the PU matrix increased nanometer surface roughness, and increased elastic modulus (TABLE 1). The elastic modulus of the 75:25 PU:CN wt % composite was over nine times the respective value measured for pure PU (100 wt %). Although the percentage elongation was similar for 100:0, 98:2, and 90:10 PU:CN wt % formulations, it was significantly lower for the 75:25 PU:CN wt %. In addition, although the tensile strength increased (from 7 to 9 MPa) for the 98:2 to 90:10 PU:CN wt %, it decreased when the fiber concentration was 25 wt % (specifically, at 5 MPa). An optimal concentration of polymer to CNs exists where the physical bond between the polymer and the CNs is at its peak and any increase in CNs from that point may weaken the material.

Characterization of mechanical and electrical property of nanomaterials: An MTS mechanical testing machine (Sintech) was used to determine the tensile strength, percentage elongation, and elastic modulus of each of the substrates (mechanical properties) pertinent to orthopedic applications. Dry, cut composite strips (40 mm×10 mm) were each tested at a strain rate of 12 mm min$^{-1}$ using a 10 lb load cell at room temperature. Resistance of the nanomaterials was determined using tetrapolar electrodes with a LRC bridge 2400. The probes were used to measure the resistance through a stack of the substrate discs and with a surface area of 1.327 cm² and heights varying from 0.035 to 0.124 cm each. Resistivity was calculated from the resistance and disc measurements (TABLE 2).

The mechanical properties of the 100 CN wt % were not measurable. The tensile strength is about an order of magnitude lower than that of cortical bone as well as other load bearing implant materials (TABLE 1) while the elastic modulus is almost three orders of magnitude lower. For these reasons, the currently designed materials would be best suited as a bone implant coating or in non-loading orthopedic applications, although future studies could perhaps optimize these mechanical properties for load bearing applications.

The electrical resistivity values of the substrates are presented in TABLE 2. Greater resistivities were measured for the 98:2 PU:CN wt % composite compared to other formulations containing CNs. The composite with 10 wt % of CNs exhibited slightly higher resistivity values than the 75:25 PU:CN wt % composite. When compared to silicon, which is commonly used in neural implant applications, the electrical resistivity of the composites disclosed herein, can be altered based upon electrical needs of an implant such as, for example, a probe. A conductive or non-conductive part of a neural prosthetic is such an implant that can be fabricated with desired resistivity levels.

The nanomaterials' effectiveness for reducing the glial scar response was tested by way of an adhesion, proliferation, phosphatase activity, and protein content assays with astrocytes, which are described as follows.

(a) Astrocyte cell culture: Rat astrocyte cells (CRC-11372) were purchased from the American Type Culture Collection. The cells were cultured in Dulbecco's Modified Eagle Medium (DMEM; Gibco), supplemented with 10% fetal bovine serum (FBS; Hyclone), and 1% penicillin/streptomycin (P/S; Hyclone) in a standard cell culture environment (37° C., humidified, 5% $CO_2$/95% air). Passages numbers 32-40 were used.

(b) Astrocyte cell adhesion assay: The astrocytes in DMEM (supplemented with 10% FBS and 1% P/S) were seeded at a density of 3,500 cells/cm² onto the substrates and were cultured in DMEM (supplemented with 10% FBS and 1% P/S) under standard cell culture conditions for one hour. Cells were then rinsed with phosphate buffered saline (PBS) to remove nonadherent cells, fixed with formaldehyde (Fisher Scientific), and stained with Hoescht 33258 dye (Sigma, St. Louis, Mo.). The visible cell nuclei were then counted in five random fields using fluorescence microscopy (365 excitation; 400 nm emission).

(c) Astrocyte proliferation assay: The astrocytes in DMEM (supplemented with 10% FBS and 1% P/S) were seeded at a density of 3,500 cells/cm² onto the substrates and were cultured in DMEM (supplemented with 10% FBS and 1% P/S) under standard cell culture conditions for 1, 3, and 5 days. Media was replaced fresh every other day. At appropriate intervals, cells were rinsed with PBS to remove nonadherent cells, fixed with formaldehyde, and stained with Hoescht 33258 dye. By counting the stained nuclei using fluorescence microscopy (365 excitation; 400 nm emission), and averaging the number of cells in five random fields per square cm of substrate, cell density was determined.

(d) Protein content assay: The astrocytes (40,000 cells/cm²) were seeded onto the substrates and cultured in DMEM (supplemented with 10% FBS and 1% P/S) under standard cell culture conditions for 7 and 14 days. Media was replaced fresh every other day. At appropriate intervals, the media was replaced with distilled water and the cells were lysed during three freeze-thaw cycles. The total intracellular protein of the lysed cells was assessed spectrophotometrically using a BCA protein assay kit (Pierce Chemical Co.) and following manufacturer's instructions. Specifically, aliquots of distilled water containing the proteins from cell lysates were incubated with a solution of copper sulfate and bicinchoninic acid for 30 minutes at 37° C. The absorbance of the samples was then measured at a light wavelength of 562 nm on a SpectraMax 290 (Molecular Devices, Corp.) with analysis software (SoftMax Pro 3.12; Molecular Devices, Corp.). The protein concentration (expressed in mg) was then determined from a standard curve obtained by running albumin concentrations in parallel with the samples.

(e) Phosphatase activity assay: The experimental substrates were seeded with astrocytes at a concentration of 40,000 cells/cm² and were cultured in DMEM (supplemented with 10% FBS and 1% P/S) under standard cell culture conditions for 7 and 14 days. Media was replaced every other day. Cells were lysed as described in the total intracellular protein content section, then the standard method of Lowry was used to resolve alkaline phosphatase activity. Aliquots of the distilled water solution containing cellular protein were incubated with a reaction solution containing 2-amino-2-methyl-1-propanol (pH=10.3) and p-nitrophenylphosphate (Diagnostic Kit #104; Sigma) at 37° C. for 15 minutes, then the reaction was terminated with 0.05 N NaOH. Light absorbance of the samples was then measured at a wavelength of 410 nm on a SpectraMax 290 (Molecular Devices, Corp.) with analysis software (SoftMax Pro 3.12; Molecular Devices, Corp.). The alkaline phosphatase activity (expressed as nano-moles of converted p-nitrophenol/min or as Sigma units) was then determined from a standard curve obtained by running known p-nitrophenol concentrations in parallel with the samples. The alkaline phosphatase activity was normalized by total intracellular protein and substrate surface area (expressed as Sigma units/mg protein/square cm).

The surface and other structural properties of nanomaterials were measure using scanning electron microscopes. Scanning electron micrographs (SEM) measurements were used to assess the topography of the substrates of interest to the present study. Samples were gold-palladium sputter-coated at room temperature. All micrographs were taken using a JEOL JSM-840 scanning electron microscope at 5 kV.

Chemical composition of the nanosubstrates was assessed at the University of Washington using electron spectroscopy for chemical analysis (ESCA). These analyses were performed on a Surface Science Instruments (SSI) X-Probe instrument. A take-off angle of 55° was used for acquisitions in the outer 10 nm of the surface. Surface Physics software (Bend, Oreg.) was used to acquire and analyze surface composition data.

Resistance of the nanomaterials was determined using tetrapolar electrodes with a LRC Bridge 2400. The probes were used to measure the resistance through a stack of the substrate discs and with a surface area of 1.327 cm² and heights varying from 0.035 to 0.124 cm each. Resistivity was calculated from the resistance and disc measurements. Data are expressed as mean values±SEM. Statistical analysis was performed using ANOVA methods to determine the variance of the quantitative data.

TABLE 1

Mechanical Properties Of Composite Materials

| Substrate (PU:CN wt. %) | Tensile Strength (MPa) | Elongation (%) | Elastic Modulus (MPa) |
|---|---|---|---|
| 100:0 | 5 | 450 | 4 |
| 98:2 | 7 | 442 | 6 |
| 90:10 | 9 | 452 | 22 |
| 75:25 | 5 | 27 | 38 |
| 0:100 | N/A | N/A | N/A |
| Cortical Bone [1] | 100 | | 10000 |
| Commercially Pure Titanium [2] | | | 110000 |
| Titanium Alloys* [2] | | | 110000-116000 |

*Values dependent on alloy composition and processing conditions.

TABLE 2

Electrical Resistivity

| Substrate (PU:CN wt. %) | Resistivity ($\Omega$-cm) |
|---|---|
| 100:0 | N/A |
| 98:2 | 20,500 |
| 90:10 | 625 |
| 75:25 | 0.354 |
| 0:100 | 0.0598 |
| Silicon* [34] | $10^{-4}$ to $10^2$ |

*Values dependent on doping and processing conditions.

TABLE 3

Average Composition of Specific Elements on Carbon Fibers of High and Low Surface Energies

| Type of Carbon Fiber | Carbon Atomic Percent | Oxygen Atomic Percent | Sulfur Atomic Percent |
|---|---|---|---|
| Conventional With Low Surface Energy | 97.5 ± 0.6 | 2.5 ± 0.6 | nd |
| Conventional With High Surface Energy | 98.6 ± 0.1 | 1.0 ± 0.2 | 0.4 ± 0.1 |
| Nanophase With Low Surface Energy | 97.0 ± 0.2 | 3.0 ± 0.2 | nd |
| Nanophase With High Surface Energy | 97.8 ± 0.4 | 1.7 ± 0.5 | 0.5 ± 0.1 | nd = not detected

DOCUMENTS CITED

The following documents are incorporated by reference to the extent they relate to protocols used in this disclosure.

Hetke, J. F. and Anderson, D. J., "Silicon electrodes for extracellular recording," In: Handbook of Neuroprosthetic Methods, (Finn and LoPresti, eds.), CRC Press LLC, pp. 163-191, 2003).

Najafi, K (1997) "Micromachined systems for neurophysiological applications.", Handbook of microlithography, micromachining, and microfabrication, Volume II: Micromachining and Microfabrication, SPIE.

Neuman et al., (1994) Fabricating Biomedical Sensors with Thin-Film Technology, IEEE EMB Mag. 13: 409-419.

Thapa et al., (2003) Nano-structured polymers enhance bladder smooth muscle cell function Biomaterials 24: 2916-26.

Wise et al., (1991) Microfabrication Techniques for Integrated Sensors and Microsystems. Science 254: 1335-1342.

U.S. Pat. No. 5,698,175
U.S. Pat. No. 6,063,243
U.S. Pat. No. 5,365,073

We claim:

1. Use of a neural implant that enhances proliferation of neural tissue and minimizes scar formation comprising:
    (a) obtaining a neural implantable device comprising a composite nanomaterial, said nanomaterial comprising carbon nanofiber material with nanofibers about 2 to 200 nm in width and a polymer matrix, wherein said nanomaterial is a polyurethane-carbon nanofiber composite, said carbon nanofibers comprise carbon nanotubes, and said carbon nanotubes are functionalized with 4-hydroxynonenal; and
    (b) securing the implantable device in the neural tissue where proliferation of neuronal tissue is desired.

2. Use of a neural implant that minimizes scar formation comprising:
    (a) obtaining a neural implantable device, wherein said neural implantable device comprises a nanocomposite component, said nanocomposite comprising a polymer material and a nanomaterial wherein said nanomaterial has a dimension ranging from 5 nm to less than 500 nm, wherein the nanomaterial component is comprised of a polyurethane (PU)-carbon nanofiber (CN) composite and the carbon nanofibers have a size in the range of about 10 to about 100 nm in width and length;
    (b) implanting said neural implantable device in the neural tissue of a patient where proliferation of neuronal tissue is desired.

3. The use in accordance with claim 2 wherein the nanofibers are multi-walled nanotubes.

4. Use of a neural implant that minimizes scar formation comprising:
    (a) obtaining a neural implantable device, wherein said neural implantable device comprises a nanocomposite component, said nanocomposite comprising a polymer material and a nanomaterial wherein said nanomaterial has a dimension ranging from 5 nm to less than 500 nm, the nanomaterial component is comprised of a polyurethane (PU)-carbon nanofiber (CN) composite, and the polyurethane (PU)-carbon nanofiber (CN) composites have a size in the range of about 50 to 100 nm and the composite comprises about 80:20 by weight percent carbon nanofiber to polyurethane;
    (b) implanting said neural implantable device in the neural tissue of a patient where proliferation of neuronal tissue is desired.

5. Use of a neural implant that minimizes scar formation comprising:
    (a) obtaining a neural implantable device, wherein said neural implantable device comprises a nanocomposite component, said nanocomposite comprising a polymer material and a nanomaterial wherein said nanomaterial has a dimension ranging from 5 nm to less than 500 nm the nanomaterial component is comprised of a polyurethane (PU)-carbon nanofiber (CN) composite, and the polyurethane (PU)-carbon nanofiber (CN) composites have a size in the range of about 60 to 100 nm and the composite comprises about 90:10 by weight percent carbon nanofiber to polyurethane;
    (b) implanting said neural implantable device in the neural tissue of a patient where proliferation of neuronal tissue is desired.

* * * * *

UNITED STATES PATENT AND TRADEMARK OFFICE
CERTIFICATE OF CORRECTION

| | | |
|---|---|---|
| PATENT NO. | : 7,993,412 B2 | Page 1 of 1 |
| APPLICATION NO. | : 10/550427 | |
| DATED | : April 9, 2011 | |
| INVENTOR(S) | : Webster et al. | |

It is certified that error appears in the above-identified patent and that said Letters Patent is hereby corrected as shown below:

In the Specification

In Column 3, Line 57, please delete "µM" and insert -- µm -- therefor.

Signed and Sealed this
Sixth Day of August, 2013

Teresa Stanek Rea
*Acting Director of the United States Patent and Trademark Office*